US006534527B2

(12) United States Patent
Wolfson et al.

(10) Patent No.: US 6,534,527 B2
(45) Date of Patent: Mar. 18, 2003

(54) EDIBLE HERBAL COMPOSITIONS FOR RELIEVING NICOTINE CRAVING

(75) Inventors: Philip Wolfson, San Anselmo, CA (US); Payton Jacobs, III, Lafayette, CA (US); Alexander T. Shulgin, Lafayette, CA (US)

(73) Assignee: Phytos, Inc., San Anselmo, CA (US)

( * ) Notice: Subject to any disclaimer, the term of this patent is extended or adjusted under 35 U.S.C. 154(b) by 0 days.

(21) Appl. No.: 09/871,693

(22) Filed: Jun. 4, 2001

(65) Prior Publication Data

US 2002/0025300 A1 Feb. 28, 2002

Related U.S. Application Data

(60) Provisional application No. 60/209,028, filed on Jun. 2, 2000.

(51) Int. Cl.[7] .......................... A61K 31/44; A61K 35/78
(52) U.S. Cl. ..................... 514/334; 514/355; 424/197.1
(58) Field of Search .............................. 424/725, 197.1; 514/334, 318, 355

(56) References Cited

U.S. PATENT DOCUMENTS 4,140,136 A * 2/1979 Geiss et al. ................... 131/17
4,817,640 A   4/1989 Summers
4,971,079 A   11/1990 Talapin et al.
5,942,244 A   8/1999 Friedman et al.

FOREIGN PATENT DOCUMENTS

EP   0146334 A2 * 6/1985   ........... A24B/15/28
SU   1268141      11/1986

OTHER PUBLICATIONS

Chamberlain, William J; (1988) Chemical Compositions of Nonsmoking Tobacco Products; J.Agric. Food Chem, vol. 36, pp. 48–50.*

Jacob et al. "Minor Tobacco Alkaloids as Biomarkers for Tobacco Use: Comparison of Users of Cararettes, Smokeless Tobacco, Cigars, and Pipes", American Journal of Public Health, 1999, vol. 89 No. 5, p. 731–736.*

* cited by examiner

Primary Examiner—Theodore J. Criares
(74) Attorney, Agent, or Firm—Richard C. Litman

(57) ABSTRACT

Compositions useful in relieving craving in nicotine habituated patients are provided that include an herbal component. The herbal component provides multiple nicotine agonists, one of which is anabasine. The compositions are preferably in the form of chewing gum, tablets, capsules, or lozenge.

16 Claims, No Drawings

EDIBLE HERBAL COMPOSITIONS FOR RELIEVING NICOTINE CRAVING

CROSS-REFERENCE TO RELATED APPLICATION

This application claims the benefit of U.S. Provisional Patent Application Ser. No. 60/209,028, filed Jun. 2, 2000.

BACKGROUND OF THE INVENTION

1. Field of the Invention

The present invention generally relates to compositions useful in relieving craving in a nicotine habituated patient who is abstaining from or reducing nicotine intake, and more particularly relates to edible compositions including an herbal component which provides multiple nicotine agonists, one of which is anabasine, but has little or no nicotine.

2. Description of the Related Art

Using 1996 data, the prevalence of cigarette smoking in the United States among adults was about 27% or 55 million people. Each year some 30% of smokers try to quit, but only about 10% are successful. The efficacy rate for formal cessation programs, defined as abstinence at one year follow-up, is between 20 and 40% of those enrolled. The most telling fact is that the majority of smokers who are successful in quitting tobacco have done so on their own. In the past ten years, 47.5% of persons attempting to quit smoking on their own were successful compared to 23.6% of those who used smoking cessation programs to quit.

There have been many therapies and pharmacologic agents used to assist in smoking cessation. Nicotine delivered through gum, transdermal patches, and nasal sprays in declining dosages over time have been the principal pharmacologic strategies, i.e., a withdrawal over time minus the tar of actual cigarettes.

More recently the anti-depressant bupropion has been reintroduced in a long acting twice-a-day preparation for smoking cessation. The anxiolytic buspirone has been suggested for use as an adjunct for the treatment of nicotine addiction. These preparations are very costly.

There have been several herbal preparations suggested for smoking cessation. A lobelia-based preparation was withdrawn because of FDA concerns sparked by toxicity reports from human use. U.S. Pat. No. 4,817,640, issued Apr. 4, 1989 to Summers, describes herbal chew and snuff products, which are said to proximate the texture, taste, and organoleptic sensation of a snuff or chew composition. The herbs are selected from dandelion, papaya, dock or sorrel, sunflower, calendula, nasturtium, mallow, chickory, corn silk, and mixtures thereof. In addition, clover is suggested for use, with red clover being the preferred major component for the snuff composition.

Among other smoking cessation products have been chewing gums that include pure anabasine in salt form. Thus, Russian Patent No. 1,268,141, published Nov. 7, 1986, describes an anti-nicotine gum formed by mixing an aqueous anabasine-HCl solution into a syrup, and formulating further with a base and sugar. U.S. Pat. No. 4,971,079, issued Nov. 20, 1990 to Talapin et al., describes another chewing gum carrier where an alkaloid, preferably anabasine hydrochloride, is coupled via a cation exchange group to a biological absorbable polymeric vehicle, and this coupled composition is then formulated in a chewing gum.

U.S. Pat. No. 5,942,244, issued Aug. 24, 1999 to Friedman et al., describes tablet formulations for local and slow release of herbal medication into the oral cavity of a subject. Anabasine and another alkaloid, anatabine, are structurally similar to nicotine, and are believed to substitute for nicotine (as agonists) at the nicotine receptor site.

SUMMARY OF THE INVENTION

In one aspect of the present invention, a composition useful in relieving craving in a nicotine habituated patient who is abstaining from or reducing nicotine intake comprises an herb or an herbal extract providing a plurality of nicotine agonists, at least one of the nicotine agonists being anabasine in an amount of at least about 0.2 weight percent of the herb or herbal extract, the herb or herbal extract having from about 0 weight percent nicotine to trace levels of nicotine therein. The composition further includes an edible carrier (e.g. solid or liquid) for the herb or herbal extract.

A preferred combination of nicotine agonists is anabasine and anatabine provided by flowers, dried leaves, stems, and/or roots, particularly of the Nicotiana glauca plant, or an herbal extract thereof. Suitable edible carriers include gums or binders (particularly for chewing gum formulations) and tableting agents (for tablet or lozenge formulation embodiments of the invention).

DETAILED DESCRIPTION OF THE PREFERRED EMBODIMENTS

Broadly, compositions of this invention are edible, that is to say, they are suitably formulated for oral use (e.g., chewing gum, tablets, lozenges, capsules, and the like). Regardless of the particular form, the compositions consist essentially of an herbal component that is derived from a plant or mixtures of plants having a quantity of anabasine and at least one other nicotine agonist, but with little or no nicotine. Among the plants from which the herbal component may be obtained are, for example, *Medicago sativa, Lupinus formosus, Solanum carolinense, Aniba coto, Zinnia elegans, Sophora pachycarpa, Verbascum songaricum, Priestleya elliptica, Priestleya tomentosa, Haloxylon persicum, Haloxylon salicornicum*, and *Nicotiana glauca*. Some species include quantities of both anabasine and nicotine, such as *N. glauca* and *N. debneyi* (with anabasine predominating).

A particularly preferred plant for obtaining the herbal component is *N. glauca* (sometimes commonly called "tree tobacco"). This is a very wide-spread plant in the United States and grows at diverse places. It has been medicinally used as an analgesic poultice applied externally. Anabasine is the dominant alkaloid in *N. glauca* leaves.

The herbal component of this invention will usually be provided by (or derived from) plant foliage (leaves and stems), although plant roots can also be used also, since the concentrations of anabasine in some plants are higher in roots than in leaves. The herbal component can be incorporated as dried plant parts or an extract therefrom. Herbal extracts are extracts of plant materials, such as a tincture of botanical materials, which typically are prepared by contacting botanical material with a solvent (British Herbal Pharmacopeia, Peter R. Bradley, Ed., British Herbal Medicine Association, 1983; and British Herbal Compendium, Peter R. Bradley, ed., British Herbal Medicine Association, 1992). The solvent, for example, can be aqueous or organic, or a combination thereof. Acceptable organic solvents include, but are not limited to, glycerin, propylene glycol or alcohol, or a combination thereof. The most preferred solvents are hydroalcoholic solvents as defined in British Herbal Pharmacopeia and Compendium.

Since a smoking cessation program may begin by gradual cessation of nicotine, followed by more complete, or by complete cessation of nicotine, inventive compositions may be formulated that have some nicotine (albeit in quantities substantially less than the anabasine amount) in which case there are an expanded number of plant sources suitable as the precursor for the herb or herbal extract. It is believed that use of an herbal component with multiple agonists to provide the essential anabasine component results in surprisingly improved properties and results over the prior attempts to use pure anabasine hydrochloride in gums or tablets. We do not presently know why the use of an herb or an herbal extract with multiple nicotine agonists provides the surprisingly improved properties and results for treating patients in a smoking reduction or cessation program. Without being limited by theory, it may be that the essential anabasine component serves as primary agonist and the one or more additional agonists, particularly such as the preferred anatabine, even when present in relatively small amounts, serves or serve as a co-agonist or co-agonists. Alternatively, it may be that there are multiple binding sites on the receptor.

In any event, use of herbs or herbal extracts in accordance with this invention provides a mixture of complex ingredients. Since an agonist stimulates the receptor by stabilizing an active confirmation, and this stabilization can be achieved in many different ways depending upon the chemical nature of the ligand and on the structure of the receptor, the combination of agonists provided from a source of complex ingredients, such as the suitable herbs or herbal extracts of this invention, may achieve a stabilizing function through multiple interactions at different parts of the target receptor.

In compositions of this invention, the anabasine content per recommended dose is in the range of between about 0.5 mg to about 10 mg, more preferably from about 2 mg to about 4 mg. Thus, for example, if a recommended daily dose is 8 tablets (as in chewing gum), then a patient could be receiving about 1–80 mg/day, more preferably 4–32 mg/day, of anabasine.

Compositions of the invention preferably have from only small, or trace, amounts of nicotine or no nicotine at all. Thus, the amount of nicotine per recommended dose will be from 0 wt. % to trace levels.

When formulated as tablets, lozenges, capsules, or chewing gum, it is contemplated that the herbal component will be present in an amount from about 200 mg to about 600 mg dry weight, or about 50 mg to 400 mg liquid extract of the dry plant material. Such compositions will typically also include additional components such as a binder, a humectant, and flavoring agents such as sweeteners, artificial or natural fruit flavors, oils, and the like. Coloring may also be included.

Thus, in one embodiment, the composition is included in a chewing gum formulation. The formulations of chewing gum are conventional, and well known to those skilled in the art. For example, a carrier may be provided that may be mixed with the herbal component. Suitable carriers, particularly in formulating chewing gums, comprise arabic, guar, and natural rubber gums. Other typical components are sweeteners (sugar, saccharin, sorbitol, aspartame), flavoring agents (e.g., mints, fruits, spices), coloring agents, and the like.

For example, the chewing gum or solid carrier may be composed, in its basic formula, of ingredients such as sucrose, corn syrup, gum base, coloring and flavoring. Ingredients such as HSH (hydrogenated starch hydrolysate), sorbitol, xylitol, and/or isomalt can replace sucrose and corn syrup at different ratios. As an example of preparation, to a hot water jacketed stainless steel gum mixer equipped with sigma tangential blades rotating at 9–12 rpm with a 1:2 rotating ratio, molten gum base may be added at approximately 55–55° C., and corn syrup or HSH, added at room temperature in the desired amounts, and mixed until fully dispersed. When a homogeneous mix is obtained, sucrose or sorbitol, xylitol, or isomalt may be added, all in powder form, and mixed until fully dispersed. During the process of the addition of the powder material, the herbal component may be added. Color, flavoring, and any other ingredient deemed necessary for the particular formula may be added. The gummy mass is then discharged from the gum mixer and conveyed to the gum forming equipment.

Thus, for example, the solid portion or chewing gum used as a carrier for the herbal component may be composed of sucrose (10–80%, preferably 15–50%), corn syrup (5–60%, preferably 10–30%), gum base (10–90%, preferably 20–80%), sorbitol (10–60%, preferably 20–50%), hydrogenated starch hydrolysate (HSH) (5–60%, preferably 10–30%), hydrolyzed proteins (1–8%, preferably 1.5–3.0%), isomalt (10–80%, preferably 15–50%), xylitol (10–80%, preferably 15–50%), artificial sweeteners (0.2–2.0%, preferably 0.5–1.0%), natural sweeteners, coloring, and flavor ingredients—to appearance and taste. Additional ingredients may include other botanical extracts, gelatin, glycerin, starch and modified starches (1–7%, preferably 1.5–5.0%), these being used for the purpose of modifying texture and chewing properties of the gum as well as to enhance the release of nicotine agonists from the gum matrix. The texture and physical properties of the finished product are affected by the final form of the chewing gum, which can also be in sugar or sugar-free form. Such a chewing gum formulation may also include a liquid center in the gum. In such case, the herbal component, preferably in the form of an herbal extract in suitable solvent, may be incorporated into or serve as the liquid center.

In another embodiment, the herb or herbal extract component of this invention is included in a tablet, capsule, or a lozenge for oral administration of the medication with local effects on the mouth and throat. Known tableting agents, binders, and the like as carriers may be used in such formulations.

Further, liquid preparations (where the carrier is a liquid) and emulsions are also contemplated for the inventive compositions.

It is to be understood that while the invention has been described above in conjunction with preferred specific embodiments, the description and examples are intended to illustrate and not limit the scope of the invention.

We claim:

1. A composition useful in relieving craving in a nicotine habituated patient who is abstaining from or reducing nicotine intake, comprising:

an herb or an herbal extract providing a plurality of nicotine agonists, at least one of the nicotine agonists being anabasine in an amount of at least about 0.2 weight percent of the herb or herbal extract, the herb or herbal extract having from about 0 weight percent nicotine to a trace amount, wherein said trace amount is less than the amount of anabasine; and an edible carrier for the herb or herbal extract.

2. The composition as in claim 1, wherein the edible carrier is a gum base.

3. The composition according to claim 1, wherein at least one of said plurality of nicotine agonists comprises an effective amount of anatabine.

4. The composition useful in relieving craving in a nicotine habituated patient according to claim 1, wherein the herb or herbal extract comprises an herb selected from the group consisting of *Medicago sativa, Lupinus formosus, Solanum carolinense, Aniba coto, Zinnia elegans, Sophora pachycarpa, Verbascum songaricum, Priestleya elliptica, Priestleya tomentosa, Haloxylon persicum, Haloxylon salicornicum*, and *Nicotiana glauca*, or an herbal extract thereof.

5. The composition useful in relieving craving in a nicotine habituated patient according to claim 1, wherein the composition comprises 200 mg to 600 mg dry weight of said herb.

6. The composition useful in relieving craving in a nicotine habituated patient according to claim 1, wherein the composition comprises 50 mg to 400 mg liquid extract of said herb.

7. The composition useful in relieving craving in a nicotine habituated patient according to claim 1, wherein the composition is made in a dosage unit selected from the group consisting of a tablet, a lozenge, a capsule, and a piece of chewing gum, and wherein said dosage unit contains between about 0.5 mg and 10 mg anabasine.

8. A composition useful in relieving craving in a nicotine habituated patient who is abstaining from or reducing nicotine intake, comprising:

an herb or an herbal extract providing a plurality of nicotine agonists, at least one of the nicotine agonists being anabasine in an amount of at least about 0.2 weight percent of the herb or herbal extract, the herb or herbal extract having from about 0 weight percent nicotine to a trace amount, wherein said trace amount is less than the amount of anabasine; and an edible carrier for the herb or herbal extract;

wherein the herb or herbal extract comprises an herb selected from the group consisting of *Medicago sativa, Lupinus formosus, Solanum carolinense, Aniba coto, Zinnia elegans, Sophora pachycarpa, Verbascum songaricum, Priestleya elliptica, Priestleya tomentosa, Haloxylon persicum, Haloxylon salicornicum*, and *Nicotiana glauca*, or an herbal extract thereof.

9. The composition useful in relieving craving in a nicotine habituated patient according to claim 8, wherein said herb or herbal extract is *Nicotiana glauca* or an herbal extract thereof.

10. The composition useful in relieving craving in a nicotine habituated patient according to claim 8, wherein said edible carrier comprises a chewing gum base having by weight:

sucrose 10–80%;

corn syrup 5–60%;

gum base 10–90%;

sorbitol 10–60%;

hydrogenated starch hydrolysate 5–60%;

hydrolyzed proteins 1–8%;

isomalt 10–80%;

xylitol 10–80%; and artificial sweeteners 0.2–2.0%.

11. The composition useful in relieving craving in a nicotine habituated patient according to claim 8, wherein the composition comprises 200 mg to 600 mg dry weight of said herb.

12. The composition useful in relieving craving in a nicotine habituated patient according to claim 8, wherein the composition comprises 50 mg to 400 mg liquid extract of said herb.

13. The composition useful in relieving craving in a nicotine habituated patient according to claim 8, wherein the composition is made in a dosage unit selected from the group consisting of a tablet, a lozenge, a capsule, and a piece of chewing gum, and wherein said dosage unit contains between about 0.5 mg and 10 mg anabasine.

14. The composition useful in relieving craving in a nicotine habituated patient according to claim 8, wherein the plurality of nicotine agonists comprises:

an effective amount of anabasine; and an effective amount of anatabine.

15. The composition useful in relieving craving in a nicotine habituated patient according to claim 8, wherein said herb or herbal extract consists essentially of between about 200 mg and 400 mg dry weight of *Nicotiana glauca*.

16. The composition useful in relieving craving in a nicotine habituated patient according to claim 8, wherein said herb or herbal extract consists essentially of between about 50 mg and 400 mg liquid extract of *Nicotiana glauca*.

\* \* \* \* \*